(12) United States Patent
Howard et al.

(10) Patent No.: US 7,410,524 B2
(45) Date of Patent: Aug. 12, 2008

(54) REGENERABLE PURIFICATION SYSTEM FOR REMOVAL OF SILOXANES AND VOLATILE ORGANIC CARBONS

(76) Inventors: Lowell E. Howard, 11206 167th Ct. NE., Redmond, WA (US) 98052; Paul M. Tower, 19524 76th Ave. SE., Snohomish, WA (US) 98296; Jeffrey V. Wetzel, 10532 Vernon Rd., Lake Stevens, WA (US) 98258

( * ) Notice: Subject to any disclaimer, the term of this patent is extended or adjusted under 35 U.S.C. 154(b) by 99 days.

(21) Appl. No.: 11/233,479

(22) Filed: Sep. 21, 2005

(65) Prior Publication Data
US 2006/0144224 A1    Jul. 6, 2006

Related U.S. Application Data

(63) Continuation-in-part of application No. 11/079,459, filed on Mar. 8, 2005, now Pat. No. 7,393,381, and a continuation-in-part of application No. 10/871,920, filed on Jun. 18, 2004, now Pat. No. 7,264,648.

(60) Provisional application No. 60/479,592, filed on Jun. 19, 2003, provisional application No. 60/611,276, filed on Sep. 21, 2004, provisional application No. 60/550,343, filed on Mar. 8, 2004.

(51) Int. Cl.
*B01D 46/46* (2006.01)
*B01D 53/12* (2006.01)
*B01D 53/02* (2006.01)
*B03C 3/68* (2006.01)

(52) U.S. Cl. .................... 95/8; 95/148; 95/109; 96/18
(58) Field of Classification Search ............. 95/18, 95/109, 8, 126; 96/112
See application file for complete search history.

(56) References Cited

U.S. PATENT DOCUMENTS

| | | | |
|---|---|---|---|
| 2,397,566 A | 4/1946 | Schutte |
| 2,590,322 A | 3/1952 | Imhoff et al. |
| 2,664,967 A | 1/1954 | Molstedt |
| 3,023,836 A | 3/1962 | Kasbohm et al. |

(Continued)

OTHER PUBLICATIONS

Schweigkofler et al. "Removal of Siloxanes in Biogas", Sep. 6, 2000, Journal of Hazardoux materials, p. 188.*

(Continued)

*Primary Examiner*—Walter D. Griffin
*Assistant Examiner*—Amber Miller-Harris
(74) *Attorney, Agent, or Firm*—Ronald M. Anderson

(57) ABSTRACT

A process to purify biogases (i.e., landfill gas and municipal digester gas), to enable such biogases to be utilized to generate electricity and heat. Biogases from these sources generally include small amounts of organosilicons (which are particularly harmful to power generation equipment, and especially harmful to micro-turbines, reciprocating internal combustion engines, and large turbines), and halogenated chemical species (which can foul expensive emission catalysts). A fluidized media bed reactor is configured to concentrate offending organics, and is coupled with another reactor vessel configured to strip the offending organics off saturated media with a hot inert gas. The removed organics are further concentrated into an inert gas stream that is conveyed to a small flare for greater than 99% destruction. The energy required to strip the organics from the spent media, and to energize the flare, is generated by the combustion of a small quantity of the purified biogas.

14 Claims, 6 Drawing Sheets

U.S. PATENT DOCUMENTS

| | | | | |
|---|---|---|---|---|
| 3,918,934 | A | * | 11/1975 | Kriebel et al. ............... 95/166 |
| 3,930,803 | A | * | 1/1976 | Winter ....................... 422/182 |
| 4,046,530 | A | | 9/1977 | Izumo et al. |
| 4,047,906 | A | | 9/1977 | Murakami et al. |
| 4,061,477 | A | | 12/1977 | Murakami et al. |
| 4,147,523 | A | | 4/1979 | Izumo |
| 4,207,082 | A | | 6/1980 | Okamoto et al. |
| 4,259,094 | A | | 3/1981 | Nagai et al. |
| 4,303,625 | A | * | 12/1981 | Cull ....................... 423/213.2 |
| 4,859,216 | A | | 8/1989 | Fritsch |
| 4,869,734 | A | | 9/1989 | Jacquish |
| 4,902,311 | A | | 2/1990 | Dingfors et al. |
| 5,176,798 | A | | 1/1993 | Rodden |
| 5,198,001 | A | | 3/1993 | Knebel et al. |
| 5,304,234 | A | | 4/1994 | Takatsuka et al. |
| 5,383,955 | A | | 1/1995 | Neal et al. |
| 5,389,125 | A | | 2/1995 | Thayer et al. |
| 5,496,395 | A | | 3/1996 | Yamazaki et al. |
| 5,676,738 | A | * | 10/1997 | Cioffi et al. ............... 95/109 |
| 5,904,750 | A | | 5/1999 | Cowles |
| 6,086,659 | A | | 7/2000 | Tentarelli ................. 96/131 |
| 6,196,050 | B1 | | 3/2001 | Ikeda et al. ............... 73/23.2 |
| 6,309,450 | B1 | | 10/2001 | Millen et al. .............. 96/131 |
| 6,372,018 | B1 | * | 4/2002 | Cowles ....................... 95/18 |
| 6,461,411 | B1 | | 10/2002 | Watanabe et al. ........... 95/116 |
| 6,706,097 | B2 | | 3/2004 | Zornes ..................... 96/153 |
| 6,770,120 | B2 | | 8/2004 | Neu et al. ................... 95/96 |
| 6,890,373 | B2 | | 5/2005 | Nemoto et al. .............. 95/90 |
| 7,025,803 | B2 | | 4/2006 | Wascheck et al. ........... 95/50 |
| 7,101,415 | B2 | | 9/2006 | Torres et al. ............... 95/115 |
| 7,264,648 | B1 | | 9/2007 | Wetzel et al. ................. 95/8 |
| 2003/0075045 | A1 | * | 4/2003 | Cowles et al. ............. 95/148 |
| 2005/0150379 | A1 | * | 7/2005 | Masetto et al. ............ 95/148 |

OTHER PUBLICATIONS

Schweigkofler et al. "Removal of Siloxanes in Biogas." Sep. 6, 2000, Journal of Hazardous Materials, p. 188.*

Applied Filter Technology, "*Fuel Cells Thrive on Clean Gas*" Chemical Engineering, Jul. 2000, http://www.appliedfiltertechnology.com/page1254.asp.

Applied Filter Technology, "*Innovative Retrofit Saves Energy*," Tax Dollars Water World, Jan. 2000. http://www.appliedfiltertechnology.com/page1255.asp.

Gary, Daniel, Acosta, Glenn, Kilgore, John, Min, Seong, Adams, Greg, Lost Angeles County Sanitation Districts Research Project to Remove Siloxanes from Digester Gas Paper presented at the California Water Pollution Controls Conference in Palm Springs, CA, Apr. 2001 http://www._appliedfiltertechnology.com/page1253.asp.

Glus, Peter H., Liang, Kit Y., P.E., Ramon, Li, P.E., Pope, Richard J., P.E., "*Recent Advances in the Removal of Volatile Methylsiloxanes from Biogas at Sewage Treatment Plants and Landfills*" Paper presented at the Annual Air and Waste Management (AWMA) 2001 Conference in Orlando, Florida. http://www._ appliedfiltertechnology.com/page1252.asp.

Glus, Peter H., Liang, Kit Y., P.E., Ramon, Li, P.E., Pope, Richard J., P.E., "*Only Three Methods to Control VMSs at Full Scale*" Scrubber Adsorber Newsletter, Feb. 2000. http://www.appliedfiltertechnology.com/page1256.asp.

Liang, Kit Y., P.E., Ramon, Li, P.E., Pirnie, Malcolm, "*Removing Siloxanes: Solution to Combustion Equipment Problems*" Paper presented at WEFTEC02 by Malcolm Pirnie Engineers and Bergen County Utility Authority, New Jersey, Oct. 2002.

Liang, Kit Y., P.E., Ramon, Li, P.E., Tudman, Scott, Schneider, Robert, J., P.E., Sheehan, Jerome F., P.E., Anderson, Eric, P.E., Pilot Testing Case Study: Pilot Testing Case Study: "*Removal of Volatile Methylsiloxanes from Anaerobic Digester Gas Fired Engines*" Paper No. 960. Paper presented at the Annual Air and Waste Management (AWMA) 1999 Conference in St. Louis, Missouri http://www.appliedfiltertechnology.com/page1257.asp.

Press Release Malcolm Pirnie, Engineers, wins "Best New Environmental Technology, Category E" ACEC 2003 Engineering Excellence Awards for SAG™ System installed at BCUA, Little Ferry, NJ, Jan. 10, 2003.

Tower, Paul, "*Removal of Siloxanes from Landfill Gas by SAG™ Polymorphous Porous Graphite Treatment Systems*" Paper presented at SWANA 26th Landfill Gas Symposium Mar. 27, 2003.

Tower, Paul, Principal Applied Filter Technology. "*New Technology For Removal of Siloxanes in Digester Gas Results in Lower Maintenance Costs and Air Quality Benefits in Power Generation Equipment.*" WEFTEC 78th Annual Technical Exhibition and Conference. Oct. 11-15, 2003. 9pp.

* cited by examiner

TYPICAL PLC PANEL
SHOWING INPUTS AND
OUTPUTS TO PROCESS

REGENERABLE PURIFICATION SYSTEM FOR REMOVAL OF SILOXANES AND VOLATILE ORGANIC CARBONS

RELATED APPLICATIONS

This application is based on a prior provisional application, Ser. No. 60/611,276, filed on Sep. 21, 2004, the benefit of the filing date of which is hereby claimed under 35 U.S.C. § 119(e). This application is further a continuation-in-part application of patent application Ser. No. 11/079,459, filed Mar. 8, 2005, which is based on a prior provisional application, Ser. No. 60/550,343, filed on Mar. 8, 2004, the benefits of the filing dates of which are hereby claimed under 35 U.S.C. § 119(e) and 120. This application is also a continuation-in-part application of copending patent application Ser. No. 10/871,920, filed Jun. 18, 2004, which is based on a prior provisional application, No. 60/479,592, filed on Jun. 19, 2003, the benefits of the filing dates of which are hereby claimed under 35 U.S.C. § 119(e) and 120.

BACKGROUND

As energy prices continue to rise, alternative energy sources become increasingly important. In particular, the use of waste methane (from renewable sources, such as municipal digesters and landfills) as a fuel is becoming increasingly widespread. Recent incentives offered by State and Federal Governments have led to the installation of more and more digester and landfill biogas power generation projects. As many developers of such projects have found, biogas is similar to crude oil in that it must be "refined" in order to use biogas as a reliable fuel. Biogas frequently contains high levels of moisture, high levels of hydrogen sulfide, and moderately high levels of halogenated contaminants. Most often, biogas also contains significant levels of organosilicons (siloxanes in particular), which are common additives to personal care products such as shaving cream, lipstick, hand cream, deodorants and hair styling products.

Combustion of organosilicons forms silicon dioxide and other silicas or silicates. Silicon dioxide is the main ingredient in sand, and such silicates can damage power generation equipment. Because of the damage inflicted by silicates, it is desirable to remove organosilicons (a source of such silicates) from biogas, to prevent such damage and prolong the life and reliability of power generation equipment. Organosilicon levels above 50 parts per billion by volume (ppbv) in biogas used as a fuel can cause severe damage to power generation equipment such as micro-turbines and turbines. Organosilicon levels above 100 ppbv in biogas used as a fuel can cause premature wear and damage to internal combustion engines used as generators.

While removal of organosilicons from biogas used as a fuel is clearly desirable, unfortunately such removal has proved to be quite challenging accomplish economically. Moreover, removal of all the organosilicons in a particular biogas is difficult, due to the wide variety of different organosilicons present in many biogas streams. Different varieties of organosilicons exhibit different molecular weights and different volatilities, complicating any removal strategy. Conventional removal methods employing activated carbon, silica gel and cold chilling lack either the ability to completely remove all of the various types of organosilicons present in a biogas stream, or are too costly. It would therefore be desirable to provide an economical technique for removing different varieties of organosilicons from biogas streams.

Non-regenerable systems, most often utilizing activated carbon or silica gel in "fixed" or stationary media beds, can only partially remove organosilicons from biogas, and even then such systems are operational only for relatively brief periods of time before requiring the media to be replaced. Activated carbon and silica gel are both negatively affected by moisture in the gas, significantly reducing their capability to remove organosilicons and almost completely eliminating their ability to remove halogenated chemical species. Moreover, highly contaminated biogases, such as those with volatile organic carbon (VOC) burdens above 400 parts per million by volume (ppmv) can cause a rapid heating of both activated carbon and silica gel media, thereby creating a dangerous condition that can lead to ignition of the organic materials picked up by the media. Non-regenerable biogas treatment systems also generate spent media, a waste product that requires replacement and disposal, generating additional expenses.

Regenerable systems employing activated carbon or silica gel, with a classical stationary "deep bed" approach (i.e., including a bed of media several feet in depth), are unwieldy to operate due to heating and cooling cycle times associated with the regeneration of the media. They are also costly to operate, due to their relatively high energy consumption. In addition, such systems generally exhibit a relatively poor removal efficiency for organosilicons and halogenated organics. Regeneration of the adsorbent media also produces a waste stream, generally a foul smelling liquid organic/water waste stream that must be disposed of at an additional cost. Disposal of such wastes further carries inherent risks of future liability if the ultimate disposal site requires cleanup. Moreover, both regenerable and non-regenerable systems employing activated carbon or silica gel in deep bed vessels require a significant amount of space, which may not be readily available. It would therefore be desirable to provide a regenerable system having a relatively small footprint, and which is capable of removing a large number of different organosilicons and VOCs, thereby minimizing any waste stream.

Another biogas treatment technique is cold chilling, which is based on the principle of lowering the temperature of the biogas to a temperature below the condensation point of the organosilicons and halogenated chemical species contained in the biogas. Such systems generally require a refrigeration unit capable of operating to as low as −20 degrees F., to effectively chill the biogas to −9 degrees F. Although these systems can remove many organosilicons and halogenated VOCs, they are ineffective on contaminants exhibiting very low boiling points and high vapor pressures. Because these systems operate below the freezing point of water, ice forms in the heat exchangers, and the heat exchangers must periodically be thawed out. For this reason, duplicate systems must be installed to provide for continuous operation. Energy consumption, expressed as a "parasitic load," is the highest with this type of biogas treatment equipment. Such systems produce a large volume of water waste and volatile chemical condensate wastes that must be disposed of at an additional cost. Furthermore, cold chilling systems also require a relatively significant amount of space for installation, which is not always readily available at potential development sites.

More recently, fluidized media bed systems have been introduced for control of VOC emissions and solvent recovery from air. Such systems generally utilize a relatively small sized particle of adsorbent material manufactured from pyrolized petroleum coke or synthetic resins. While effective for solvent recovery and to remove VOCs from air, such systems are not particularly effective at removing organosilicons and halogenated organics from biogas. In general, systems configured to remove contaminants from air include components than cannot readily withstand the harsh chemical conditions associated with the processing of biogas. As a result, rapid corrosion and failure of key components occurs. Furthermore, the moisture present in biogas can cause the relatively small adsorbent particles in such systems to conglomerate, degrading the fluidity of the media bed, which leads to system failure. In addition, an outside fuel source must be utilized to destroy the organics once they are removed from the air stream, or energy must be used to condense the removed organics so they may be re-used or disposed of as a liquid waste stream.

Because such air purification technology is designed for relatively low pressure or ambient (i.e., atmospheric) pressure streams, the equipment cannot withstand the higher biogas pressures required by many types of power generation equipment. Even at relatively low pressures, distortion of rectangular process equipment components occurs, resulting in gas leaks. Biogas leaks pose several problems. Since biogas is a fuel and has a commercial value, gas leaks in treatment equipment can be expensive, as well as being dangerous. Biogas is also highly odiferous, containing condensable organics referred to as "skunk oil." Thus, it is desirable to prevent gas leakage.

A significant drawback of existing fluidized media bed technology is a lack of adequate automation. Most projects involving the combustion of biogas for power generation require biogas systems to be operational with less than a 5% downtime. It would therefore be desirable to develop automated systems capable of operating with minimal downtime.

A drawback of the biogas treatment systems discussed above is that they generally are not able to attain the high purity level required by most biogas combustion equipment. Thus, it would be desirable to provide for a nominally complete removal of organosilicons and halogenated volatile chemicals.

SUMMARY

A novel approach for removing organosilicons and halogenated chemical species from biogas using a single treatment system. Removal of organosilicons will reduce damage to power generation equipment caused by silica and silicates. Removal of halogenated chemical species will reduce damage to expensive emission catalysts. The basis for this treatment technology is a fluidized media bed reactor, configured to concentrate offending organics, coupled with another reactor vessel configured to strip the offending organics off the media with a hot inert gas. The removed organics are further concentrated into an inert gas stream that is conveyed to a small flare for greater than 99% destruction. The energy required to strip the organics from the spent media, and to energize the flare, is generated by the combustion of a small quantity of the purified biogas. Empirical studies indicate a biogas purified using such techniques contains less than 50 ppbv organosilicons and halogenated organics, and the cleaned biogas is suitable for use as a fuel in many types of power generation equipment, including methane fuel cells. The cleaned biogas can be safely transported in industrial and commercial pipelines.

The primary use of the technique disclosed herein is to purify gaseous fuels, and in particular, biogas (municipal anaerobic digester gas and landfill gas).

A key feature of the technique and system disclosed herein is their ability to remove organosilicons and halogenated chemicals from biogas, to protect power generation and emission abatement equipment.

A second key feature of the technique and system disclosed herein is their ability to process a large volume of biogas in a system of relatively small size.

A third key feature of the technique and system disclosed herein is their ability to prevent flammable and odorous gas leakage, and to facilitate recovery and disposition of same.

A fourth key feature of the technique and system disclosed herein is their ability to control an adsorbent media recycle rate, where media is transferred from a concentrator vessel to a regeneration vessel and back again, by the use of single rotary gas-tight valves, or dual gas-lock valves.

A fifth key feature of the technique and system disclosed herein is their ability to sense and control oxygen content in a concentrated, stripped VOC gas stream, to minimize a possibility of the formation of explosive conditions.

A sixth key feature of the technique and system disclosed herein is a logic-based control system for automating the process and system.

A seventh key feature of the technique and system disclosed herein is the employment of a fiber optic sensing system for measurement and control of adsorbent media levels at critical locations in the processing equipment.

An eighth key feature of the technique and system disclosed herein is the utilization of the biogas itself to provide the energy to strip and concentrate the biogas contaminants into a separate waste stream.

A ninth key feature of technique and system disclosed herein is the utilization of the biogas itself to provide energy for the destruction of the stripped biogas contaminants in a small enclosed ground flare.

A tenth key feature of the technique and system disclosed herein is the production of ultra-pure biogas for use in applications requiring high purity (i.e., a very low contaminant level) biogas, such as turbine-driven generators, pipelines, and fuel cells.

An eleventh key feature of the technique and system disclosed herein is enabling operational downtimes of less than about 5% to be achieved.

A twelfth key feature of the technique and system disclosed herein is the utilization of heat produced by the process to pre-condition the gas to be treated.

A thirteenth key feature of the technique and system disclosed herein is a low energy consumption rate, as measured by a parasitic biogas utilization rate of less than about 0.5% by volume.

A fourteenth key feature of the technique and system disclosed herein is enabling biogas to be processed at elevated pressures without gas leaks.

An exemplary process for removing organosilicon and halogenated contaminants from a gas stream to achieve a clean fuel gas disclosed herein includes the steps of passing the gas stream through a filter vessel including a filter media configured to remove organosilicon and halogenated contaminants from the gas stream, thereby producing a clean fuel gas and spent filter media, removing a portion of the spent filter media from the filter vessel, using a portion of the clean fuel gas to generate a hot inert gas, using the hot inert gas to remove contaminants from the spent filter media, thereby regenerating the filter media, returning the regenerated filter media to the filter vessel, and using a portion of the clean fuel gas to treat the contaminants removed from the spent filter media.

An exemplary system for removing organosilicon and halogenated contaminants from a gas stream to achieve a clean fuel gas disclosed herein includes a filter vessel including a filter media configured to remove organosilicon and halogenated contaminants from the gas stream, thereby producing a clean fuel gas and spent filter media, a regeneration vessel configured to remove contaminants from spent filter media, a filter media transfer subsystem configured to transfer spent filter media from the filter vessel to the regeneration vessel, and to transfer regenerated filter media from the regeneration vessel to the filter vessel, a hot inert gas generator configured to use a portion of the clean fuel gas to generate a hot inert gas, the hot inert gas generator being coupled in fluid communication with the filter vessel to receive the clean fuel gas, and with the regeneration vessel, to direct hot inert gas into the regeneration vessel to regenerate the spent filter media, and a flare subsystem configured to use a portion of the clean fuel gas to treat contaminants removed from the spent filter media by the hot inert gas, the flare subsystem being coupled in fluid communication with the filter vessel to receive the clean fuel gas, and with the regeneration vessel to receive the hot inert gas loaded with contaminants removed from the regenerated filter media.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 5C:
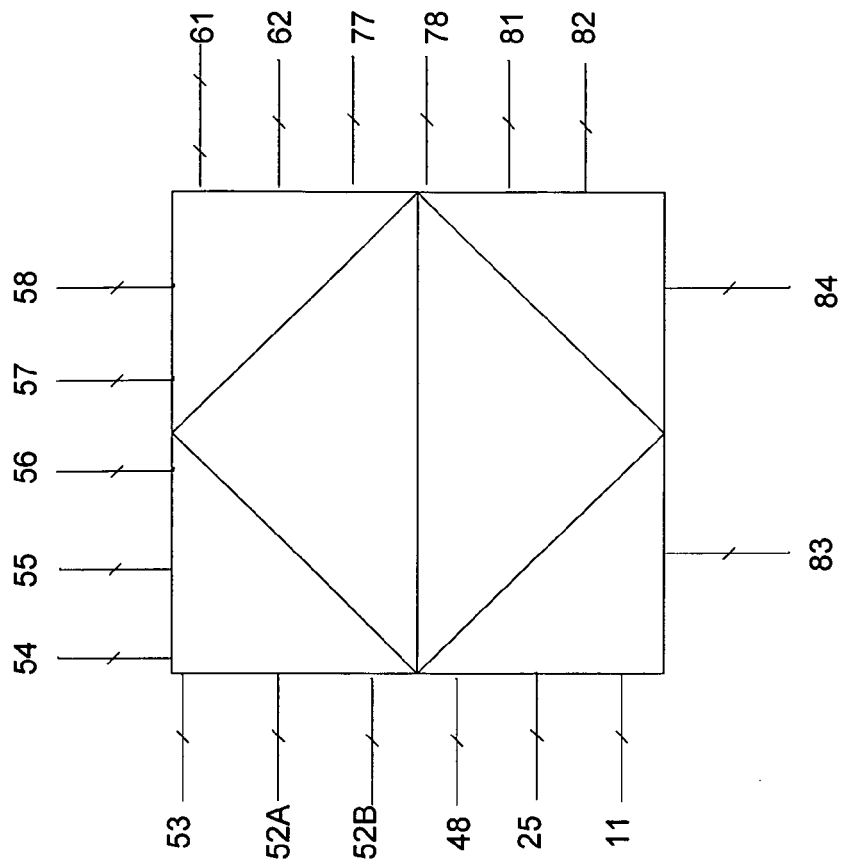
Figure 5B:
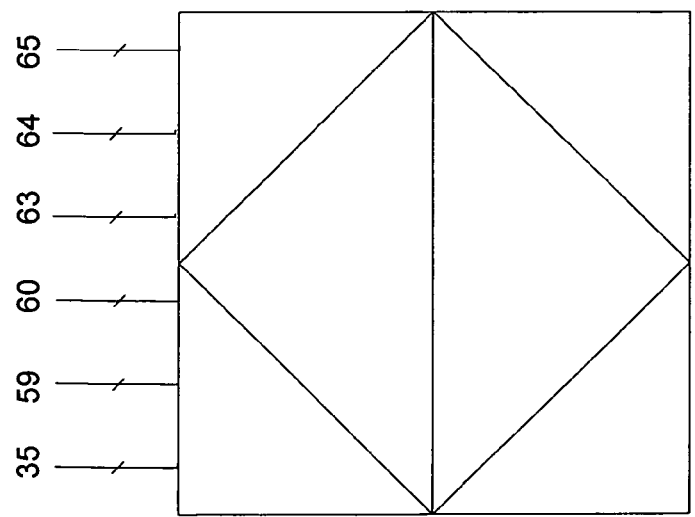
Figure 6:
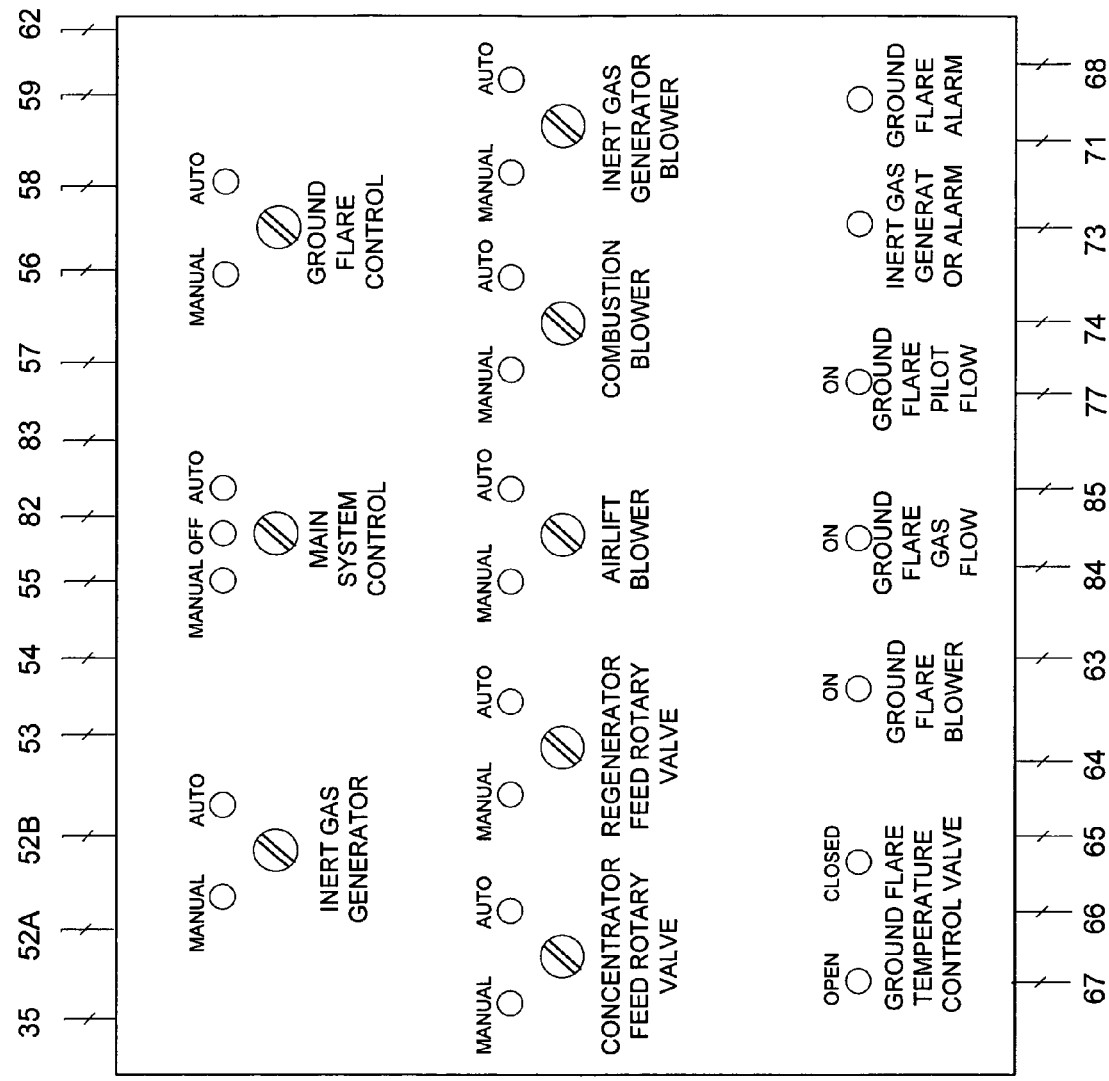

FIG. 5A schematically illustrates logical inputs for automation of the ground flare from start up to shut down;

FIG. 5B schematically illustrates logical inputs for automation of the inert gas generator from start-up to shut down; and FIG. 5C schematically illustrates logical inputs for process automation from start-up to shut down;

FIG. 6 schematically illustrates an exemplary panel cover with inputs from the various process components.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

Overview of the Disclosure Provided Herein

As discussed above, biogas and digester gas frequently include organosilicons and halogenated chemical species. When such gas is combusted, the organosilicons are converted to very abrasive silicates, which can cause extensive damage to electrical power generation equipment. The halogenated chemical species can poison expensive emissions catalysts. Disclosed herein are methods and systems for removing organosilicons and halogenated chemical species using a single system exhibiting a relatively small footprint and a minimal parasitic load.

Figure 1:
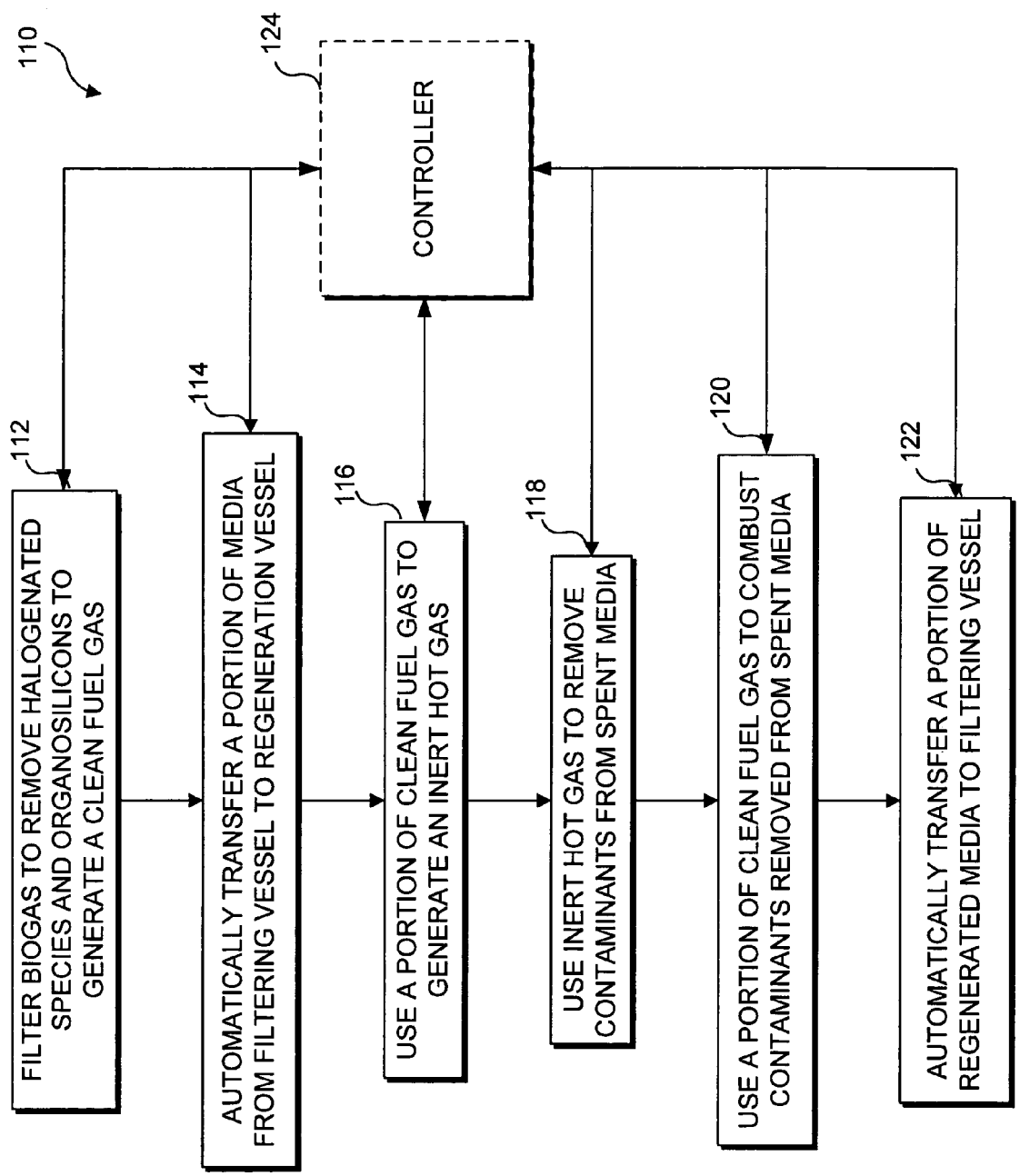
FIG. 1 is a flowchart which illustrates the overall sequence of steps utilized in an exemplary method to remove organosilicon and halogenated contaminants from a gas stream to achieve a clean fuel gas suitable for use in electrical power generation equipment.

FIG. 1 is a flowchart 110 including exemplary method steps for removing organosilicons and halogenated chemical species from a fuel gas stream (such as biogas or digester gas). In a step 112, the dirty fuel gas is filtered to remove organosilicons and halogenated chemical species, thereby generating a clean fuel gas and spent filter media. Details of preferred filter media are provided below. In a step 114, a portion of spent filter media is automatically transferred to a regeneration vessel. In a preferred implementation, pneumatic subsystems are used to move filter media back and forth between a filter vessel and the regeneration vessel. In a step 116, a portion of the clean fuel gas is combusted to generate a hot inert gas (i.e., exhaust gas containing low levels of oxygen). In a step 118, the hot inert gas is used to remove contaminants from the spent filter media. In a step 120, a portion of the clean fuel gas is used treat the hot inert gas laden with contaminants removed from the spent filter media. In a step 122, a portion of the regenerated filter media is returned to the filter vessel, such that additional quantities of dirty fuel gas can be treated. Significantly, this technique uses cleaned fuel gas for generating the hot inert gas and destroying the removed contaminants, achieving a method for removing organosilicons and halogenated chemical species from a fuel gas stream that has a minimal parasitic load. A controller 124 is preferably configured to automate the process.

Figure 2:
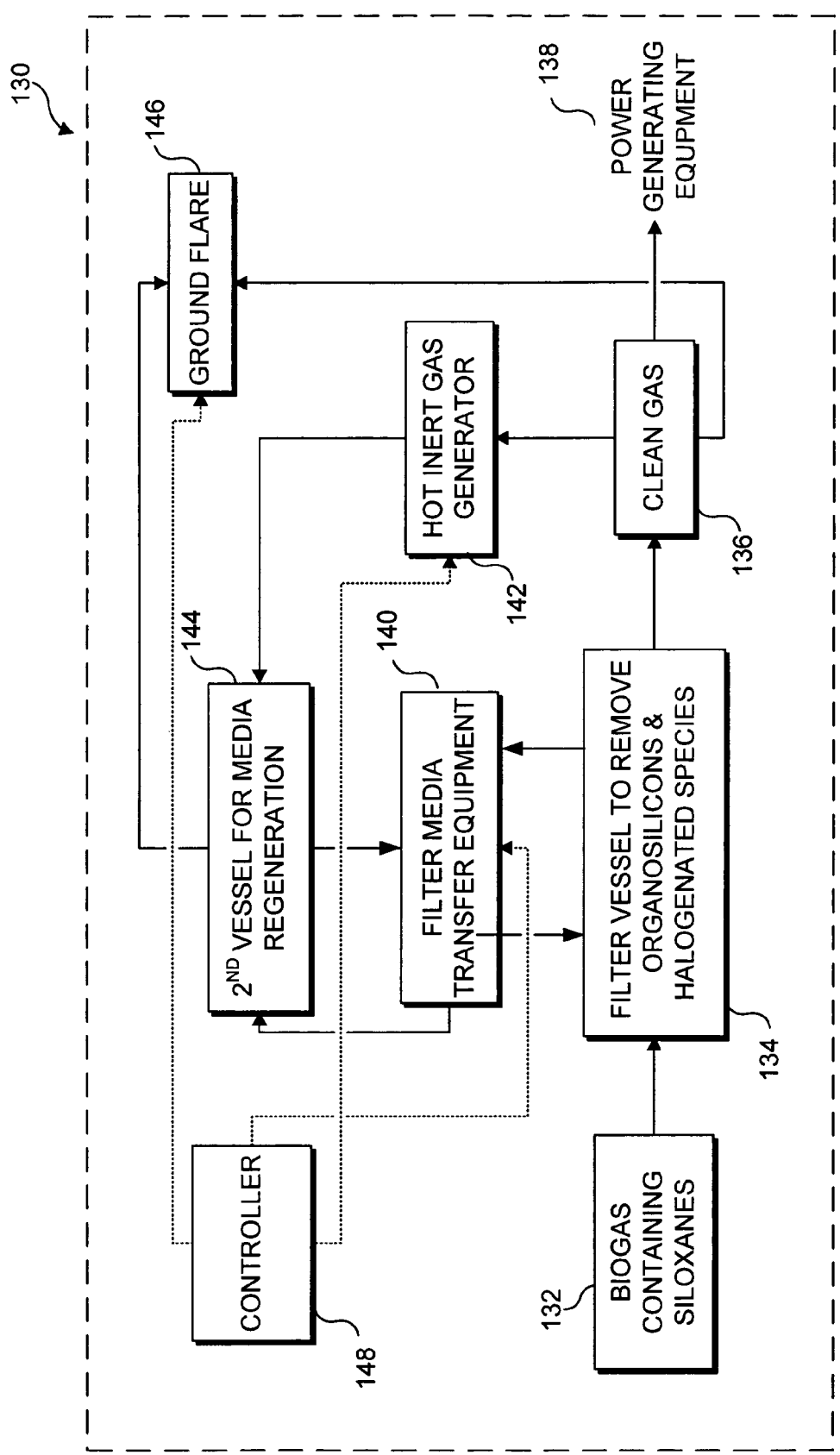
FIG. 2 is a block diagram of an exemplary system for removing organosilicon and halogenated contaminants from a gas stream to achieve a clean fuel gas suitable for use in electrical power generation equipment.

FIG. 2 is a block diagram of an exemplary system 130 configured to remove organosilicons and halogenated chemical species from a fuel gas stream (such as biogas or digester gas). A biogas stream 132 (or digester gas, or some other fuel stream contaminated with organosilicons and halogenated chemical species) is directed into a filter vessel 134, which includes filter media configured to remove organosilicons and halogenated chemical species, thereby generating a clean fuel gas 136 and spent filter media. A portion of clean fuel gas 136 is preferably conveyed to power generating equipment 138, although it should be understood that the clean fuel gas can be stored for later use, or conveyed to other types of processing equipment needing a filtered fuel gas. System 130 includes a filter media transfer subsystem 140, configured to move filter media between filter vessel 134 and a regeneration vessel 144. Spent filter media moves from filter vessel 134 to regeneration vessel 144 to be regenerated, while regenerated filter media is transferred from regeneration vessel 144 to filter vessel 134 for reuse. A hot inert gas generator 142 uses some of clean gas 136 to generate a hot inert gas. As will be described in greater detail below, hot inert gas generator 142 is configured to generate an exhaust gas that is sufficiently depleted of oxygen so as to reduce any chance of causing a fire or explosion in regeneration vessel 144. The hot inert gas from hot inert gas generator 142 is passed through the spent filter media in regeneration vessel 144, thereby stripping the contaminants from the spent filter media and regenerating the filter media. The hot inert gas laden with contaminants is then directed to a ground flare 146, which uses some of the clean fuel gas to combust the hot inert gas and contaminants, according to accepted environmental practices (greater than 99% destruction). Significantly, the energy required to strip the organics from the spent media, and to energize the flare, is generated by the combustion of a small quantity of the purified biogas. Empirical studies indicate a biogas purified using such techniques contains less than 50 ppbv organosilicons and halogenated organics, and the cleaned biogas is suitable for use as a fuel in many types of power generation equipment, including methane fuel cells. The cleaned biogas can be safely transported in industrial and commercial pipelines. A controller 148 is logically coupled to filter media transfer equipment 140, hot inert gas generator 142, in ground flare 146, to facilitate automated operation of the system.

Figure 3:
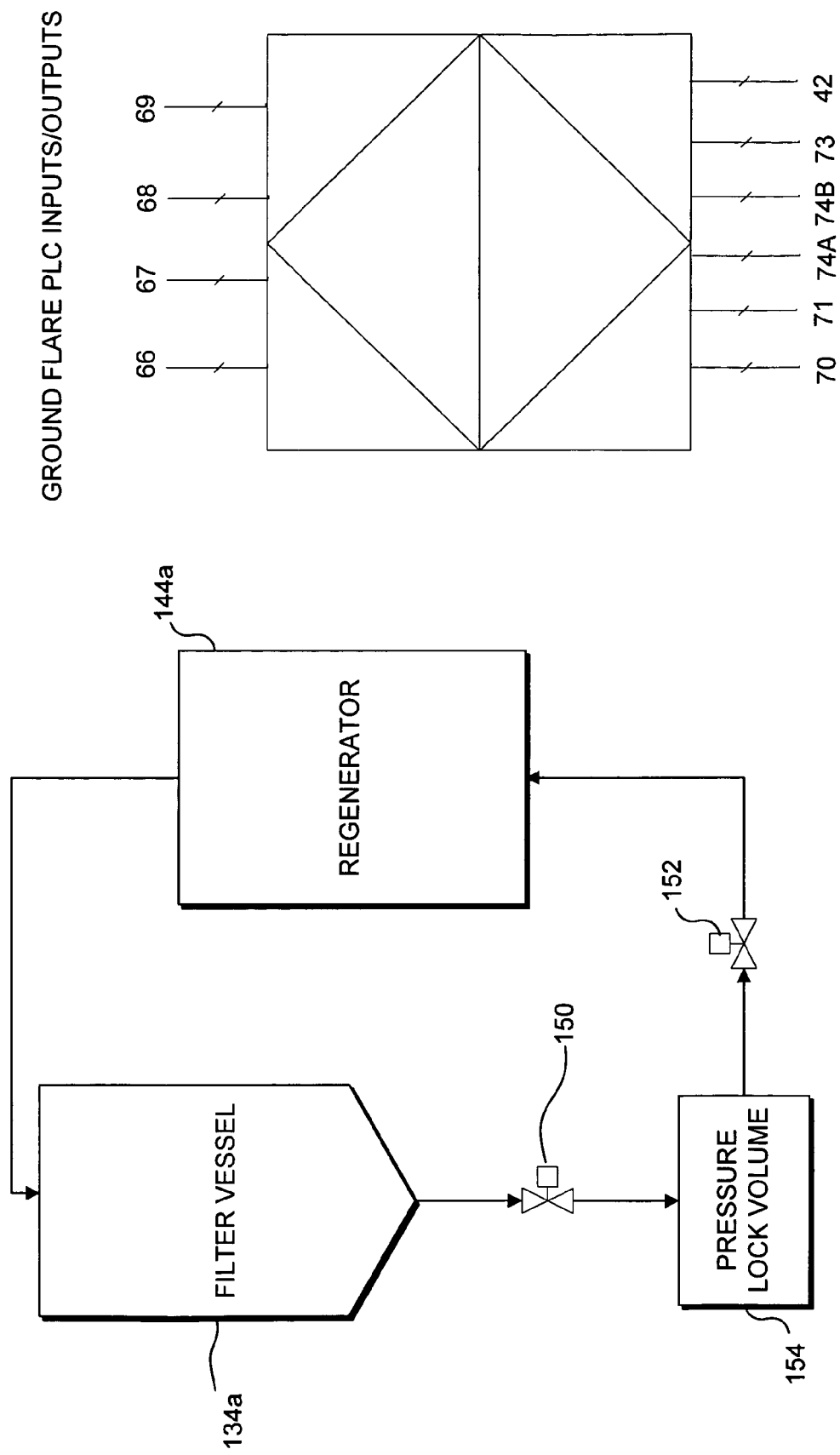
FIG. 3 is a block diagram schematically illustrating a modification to the system of FIG. 2 which enables leak proof operation to be achieved even with relatively high gas stream pressures.

Incoming dirty fuel gas streams can have widely varying pressures. FIG. 3 schematically illustrates a modification of system 130 to enable the system to safely accommodate relatively high pressure dirty fuel gas streams. A pressure lock volume 154 is disposed between a filter vessel 134a and a regeneration vessel 144a (filter media transfer equipment have been eliminated from this figure to simplify the drawing, although it should be understood that such filter media transfer equipment are included). A valve 150 is configured to selectively place pressure lock volume 154 in fluid communication with filter vessel 134a. A valve 152 is configured to selectively place pressure lock volume 154 in fluid communication with regeneration vessel 144a. Valves 150 and 152 are capable of leak proof operation even under relatively high pressures. With valve 152 closed, valve 150 is opened to transfer a portion of spent media from filter vessel 134a into pressure lock volume 154. Valve 150 is then closed, and valve 152 is opened to transfer the spent filter media from pressure lock volume 154 into regeneration vessel 144a. Pressure lock volume 154 isolates filter vessel 134a from regeneration vessel 144a, such that only filter vessel 134a needs to be configured to operate under high pressures. A similar pressure lock volume is used to transfer regenerated filter media from regeneration vessel 144a back into filter vessel 134a for reuse.

Preferred Filter Media

The techniques and system described herein can utilize several different types of filter media. Conventional filter media include carbon based adsorbents and silica gel based adsorbents. Because the filter media will be transferred back and forth between the filter vessel and the regeneration vessel, preferred filter media will have a size and shape facilitating transfer of the filter media back and forth between the filter vessel and the regeneration vessel. Furthermore, preferable filter media will be abrasion resistant, to minimize the amount of dust or fines generated during the transfer process.

Particularly preferred filter media include, but are not limited to, spherical pyrolized carbonaceous adsorbents, such as those available from the Kureha Chemical Company, spherical synthetic adsorbent resinous materials, and spherical synthetic silica and mineral based adsorbents (available from Applied Filter Technology, Inc., Snohomish Wash.). Such media are generally spherical, have diameters ranging from about 0.2 mm to about 3.5 mm, and are abrasion resistant. Additional media types that may be used include polymorphous graphite pellets (also available from Applied Filter Technology), activated carbon in pellet or granular form, silica gels, zeolites, and other adsorbent media of small particle size, nominally from about 0.5 mm to about 3 mm. These additional media types are preferably characterized by high hardness and resistance to abrasion. Such media are described in greater detail in the following copending and commonly assigned U.S. patent application Ser. No. 11/079,459, entitled Removing Siloxanes from a Gas Stream Using a Mineral Based Adsorption Media, filed Mar. 8, 2005, and Ser. No. 10/871,920, entitled Removing Siloxanes from a Gas Using a Segmented Filtration System Customized to the Gas Composition, filed Jun. 18, 2004, the specification and disclosure of which are hereby specifically incorporated by reference.

Detailed Description of an Exemplary Low-Pressure System

Figure 4:
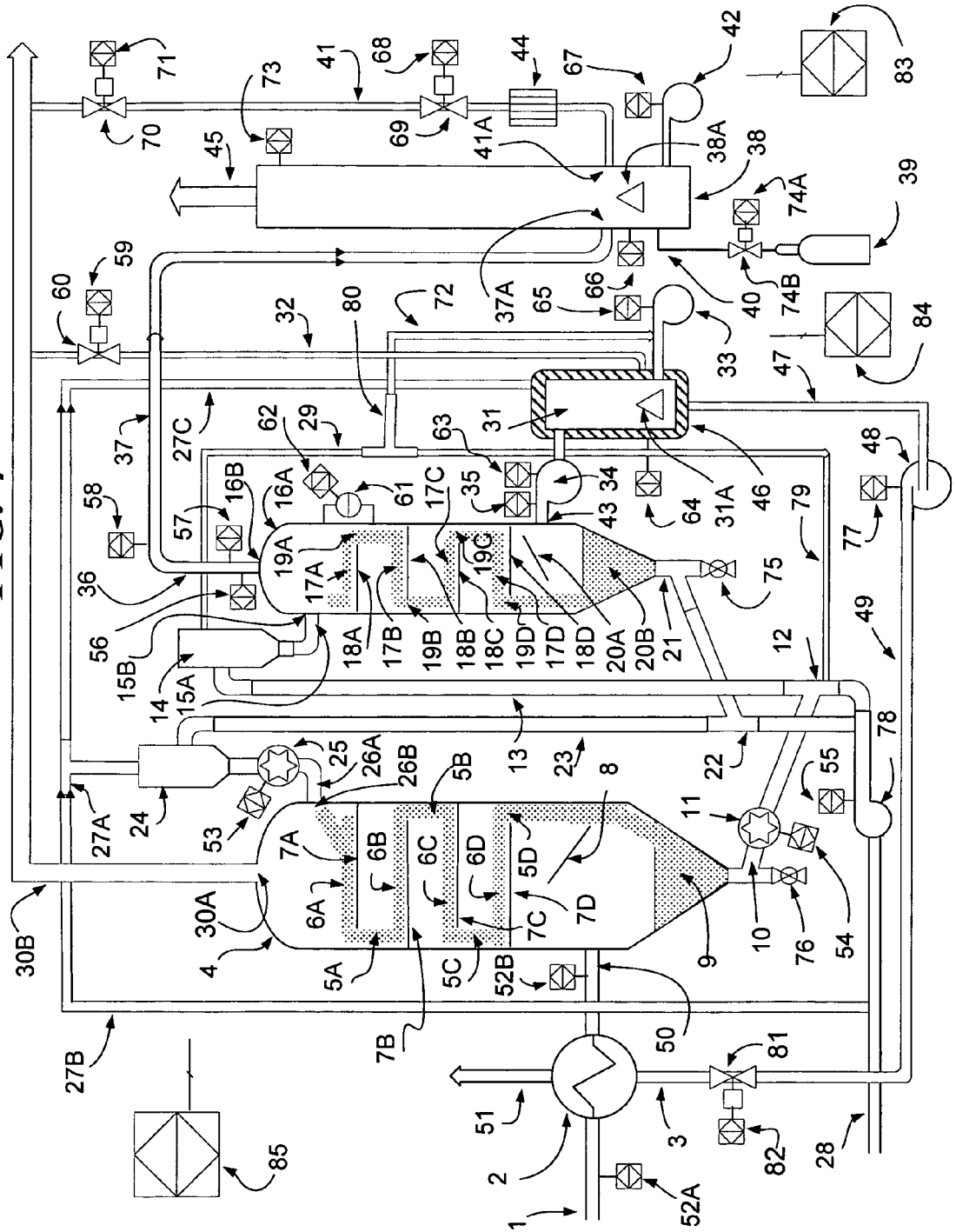
FIG. 4 is a detailed process diagram illustrating an exemplary low pressure system based on the exemplary system of FIG. 2, including a fluidized media concentrator, a fluidized media regenerator, a pneumatic media transfer component including two gas lock rotary valves, an inert gas generator, a heat exchanger, an enclosed ground flare, and a control system for automation.

FIG. 4 illustrates the overall process components and interconnectivity for system and method disclosed herein. Referring to FIG. 4, there are five distinct main process operations encompassed in the present disclosure. The first of these is a process whereby the biogas contaminants are concentrated onto a regenerable media in a concentrator 4. A second process involves a pneumatic conveyance of the media from concentrator 4 to a regenerator 16, and back to concentrator 4. A third process involves stripping the concentrated contaminants from the spent media in regenerator 16. A fourth process is the production of a hot inert regenerant gas by an Inert Gas Generator 31, for use by regenerator 16. A fifth process is the destruction of the spent regenerant gas stream in a small enclosed ground flare 38.

In an exemplary system three Programmable Logic Controllers (PLCs) control the entire process. Ground flare 38 is controlled by a separate PLC 83, and inert gas generator 31 (IGG 31) is controlled by a separate PLC 84, each of which are interlinked to a main PLC 85, which controls all of the system components.

The Concentration of Biogas Contaminants

Contaminated biogas from the gas source enters the Biogas Purification System through a suitably sized pipe 1, and is conveyed first to a heat exchanger 2, which elevates the temperature of the gas approximately 20° F. to reduce its ability to condense water vapor. This heat exchanger receives heated air from a heat jacket 46 incorporated into inert gas generator 31, by means of a blower 48 via pipe 49 (an uncontrolled flow) and pipe 3 (a controlled flow). After the hot air is used in the heat exchanger, it is passed to the atmosphere through a vent pipe 51. The contaminated biogas exits heat exchanger 2 and proceeds to a bottom side inlet 50 of concentrator vessel 4 (a generally cylindrical stainless steel cone bottom vessel with a dish top, able to withstand pressures above atmospheric). After entering concentrator vessel 4, the contaminated biogas flows upward around a baffle 8 (to divert it away from a spent media flow, described in detail below), then through a series of horizontally mounted perforated trays numbering from four to eight or more (FIG. 4 illustrates a configuration utilizing four perforated trays, although the number of trays shown is intended to be exemplary, rather than limiting). Perforated trays 7A-7D each support a layer of adsorbent media 6A-D, nominally one to two inches in depth (such dimensions are intended to be exemplary, rather than limiting). The upward flow of the contaminated biogas through perforated trays 7A-7D and adsorbent media layers 6A-6D is at a prescribed velocity, which causes media layers 6A-6D to acquire a semi-fluidized state. This state of semi-fluidization causes the media 6A to flow horizontally toward one side of its corresponding perforated tray 7A, where there is an opening 5A. Once the fluidized media reaches opening 5A at the side of perforated tray 7A, the media is no longer fluidized, and the media falls through opening 5A to tray 7B, where it is re-fluidized (as indicated by media layer 6B). Media layer 6B similarly flows to an opening 5B in tray 7B. Again, once the fluidized media in tray 7B reaches opening 5B, the media is no longer fluidized and falls through the opening to the tray below. This process repeats through trays 7C and 7D (with media passing through an opening 5C in tray 7C to reach tray 7D), until the filter media falls through an opening 5D in tray 7D, and flows by gravity into an internal reservoir 9, where it is collected and stored.

The flow of adsorbent media with respect to the biogas flow is countercurrent. As the biogas flows upward through the perforated trays 7A-7D (containing the adsorbent media), more and more contaminants are removed, and the biogas becomes cleaner and cleaner. As the filter media moves media downward through perforated trays 7A-7D, the filter media becomes more and more contaminated (i.e., filter media layer 6D is more contaminated than filter media layer 6A). As the adsorbent media picks up more and more of the contaminants from the biogas, its density increases. The treated biogas exits the concentrator vessel through an opening 30A the top center of concentrator vessel 4 and is conveyed to power generation or combustion equipment through a pipe 30B having the same diameter as inlet pipe 1.

Adsorbent Media Transport

From spent media internal reservoir 9 in the bottom of concentrator vessel 4 the spent adsorbent media flows by gravity through a "Y" pipe junction 10 to the inlet of a spent media motor-driven rotary valve 11, which prevents gas leakage from concentrator vessel 4, and which controls the flow rate of the media. Note that rotary valves generally leak at pressures greater than about 1.5 PSI, thus the system of FIG. 4 is intended to be used with relatively the pressures. Different valve configurations, generally discussed above with respect to FIG. 3, can be implemented for higher pressures. The spent media then continues to flow by gravity through a media conduit leg of "Y" pipe junction 10 to the inlet of a spent media transport venturi 12, which receives air from an pneumatic blower 78. The internal configuration of venturi 12 and the motive air from pneumatic blower 78 substantially fluidizes the spent media, forcing the spent media to travel vertically upward through a spent media transfer pipe 13, to a small spent media receiving vessel 14, at which point the spent media is no longer fluidized. From small spent media receiving vessel 14 the spent media flows downward by gravity through a pipe 15A into a top side inlet 15B of a regenerator vessel 16A.

The regenerated media (the process of regenerating the media is described in greater detail below) is returned to concentrator vessel 4 in the following manner. From a regenerated media reservoir 20B in the bottom of the regenerator vessel 16A, the regenerated media flows by gravity through a "Y" pipe junction 21 to the inlet of a regenerated media venturi 22, which receives air from pneumatic blower 78. The internal configuration of venturi 22 and the motive air from pneumatic blower 78 substantially fluidizes the regenerated media, forcing it to travel vertically upward through a regenerated media transfer pipe 23 to a small regenerated media receiving vessel 24, where the regenerated media is no longer fluidized. A length of regenerated media transfer pipe 23 and an air flow volume from pneumatic blower 78 are configured to provide cooling to the regenerated media, so that when it arrives at regenerated media receiving vessel 14, the regenerated media is substantially at ambient temperature. From small spent media receiving vessel 14, the regenerated media flows downward by gravity through a pipe 26A into a top side inlet 26B of concentrator vessel 4.

The prevention of gas leaks and odors escaping from the purification system via spent media receiving vessel 14 is accomplished by recycling part of spent media pneumatic transport air through a spent media transport air return pipe 29 and a spent media transport air return pipe "T" junction 80. At spent media transport air return pipe "T" junction 80, part of the spent media pneumatic transport air is conveyed to an inlet of an IGG combustion air blower 33, through spent media air return pipe 29 to an IGG combustion air blower intake pipe 72. Part of the spent media pneumatic transport air is conveyed to the inlet of spent media transport venturi 12, which provides for a closed loop to prevent leakage of odors and transport air to the atmosphere.

The regenerated media transport air is vented into a "T" pipe 27A, where part of it is returned through a pipe 27B to the inlet of pneumatic blower 78. The remainder of the regenerated media transport air is conveyed through a pipe 27C to heat jacket 46 of IGG 31. This air is used to cool IGG 31, and after the air absorbs heat from IGG 31, the heated air is conveyed through a pipe 47 to an inlet of a hot air blower 48 for transport through a pipe 49 and a hot air flow control valve 81 to heat exchanger 2, discussed above. After heat has been transferred from the heated air to the incoming biogas, the air is discharged from heat exchanger 2 to the atmosphere through vent pipe 51.

Spent Adsorbent Media Regeneration

After entering regenerator vessel 16A, the spent media falls onto an uppermost perforated tray 18A, then through a series of horizontally mounted perforated trays 18A-18D, numbering from four to eight or more (it should be recognized that the number of trays shown is intended to be exemplary, rather than limiting). Perforated trays 18A-18D each support a layer of spent adsorbent media (i.e., layers 17A-17D), nominally one to two inches in depth (such dimensions are intended to be exemplary). An upward flow of hot inert gas through perforated trays 18A-18D and spent adsorbent media layers 17A-17D is at a prescribed velocity, which causes spent media layers 17A-17D to acquire a semi-fluidized state. This state of semi-fluidization causes spent media in layer 17A to flow horizontally toward one side of perforated tray 18A, where an opening 19A is disposed. Once the media in layer 17A reaches opening 19A, the spent media is no longer fluidized and falls through opening 19A to the next perforated tray (i.e., perforated tray 18B), where it is re-fluidized in layer 17B. The spent adsorbent media in layer 17B then commences its flow in a direction countercurrent to the flow of media in layer 17A on perforated tray 18A. The spent adsorbent media in layer 17B moves toward an opening 19B at the side of perforated tray 18B. When the spent adsorbent media reaches opening 19B, it is no longer fluidized and falls through the opening to perforated tray 18C, where it is similarly re-fluidized. This process repeats, and spent absorbent media in layer 17C moves to an opening 19C in perforated tray 18C, where the spent adsorbent media falls through opening 19C to reach perforated tray 18D. Similarly, spent absorbent media in layer 17D moves towards an opening 19D in perforated tray 18D. The spent absorbent media falls through opening 19D and flows by gravity into internal reservoir 20B, where it is collected and stored. The media collected and stored in the internal reservoir is now regenerated.

The flow of spent adsorbent media with respect to the hot inert regenerant gas flow is countercurrent. The hot inert regenerant gas enters the regenerator vessel through a hot inert gas inlet 43 and flows upward around a baffle 20A, to divert it away from the (now regenerated) media flow from opening 19D in bottom perforated tray 18D. As the hot inert regenerant gas flows upward through perforated trays 18A-18D, containing spent absorbent media in layers 17A-17D, the hot inert regenerant gas becomes more and more saturated with the contaminants, while the spent adsorbent media layers 17A-17D becomes more and more purged of the contaminants, as the spent absorbent media progresses from uppermost perforated tray 18A, downward past bottom perforated tray 18D, and into spent media reservoir 20B at the bottom of regenerator vessel 16A. As the adsorbent media in layers 17A-17D is increasingly purged of contaminants in its journey through regenerator vessel 16A, its density decreases. The spent hot inert regenerant gas (now referred to as "concentrated waste gas") exits the regenerator vessel through an opening 16B in the top center of the regenerator vessel 16A, and is conveyed into a concentrated waste gas outlet pipe 36. From concentrated waste gas outlet pipe 36 the concentrated waste gas is conveyed through a pipe 37 to a small enclosed ground flare 38 for destruction.

Production of a Hot Regenerant Gas

Regenerator vessel 16A receives hot inert gas from IGG 31, which provides the energy to strip the contaminants from the spent adsorbent media. In order to generate the hot inert gas, IGG 31 receives purified biogas through a pipe 72, which is mixed with air from Inert Gas Generator Combustion Air Blower 33, and combusts this biogas/air mixture in an internal burner 31A. Internal Burner 31A is specially designed to effectively burn biogas that is nominally 35% methane to 75% methane. The hot, inert gas is drawn from IGG 31 by a Hot Inert Gas Fan 34, which boosts a pressure of the hot inert gas before it enters regenerator vessel 16A. PLC 84 is configured to maintain a temperature of nominally between about 400° F. and about 550° F., and a volumetric flow commensurate with the internal dimensions of regenerator vessel 16A.

Significantly, the hot inert gas is not simply hot air, but rather a mixture of hot carbon dioxide, nitrogen, and water vapor. Preferably PLC 84 is configured to control the oxygen level of the hot inert gas generated to nominally range from about 0.5% by volume to less than about 4% by volume. If the oxygen level in the hot inert gas is not properly controlled, a large volumetric flow of hot inert gas would be required to prevent potentially explosive conditions from being generated. Controlling the oxygen content in the hot inert gas reduces an amount of purified biogas consumed by IGG 31, as well as an amount of purified biogas consumed by ground flare 38, enhancing the overall economics of the system.

Destruction of the Stripped Contaminants Using an Enclosed Ground Flare

The hot inert gas strips the contaminants from the spent adsorbent media in regenerator vessel 16A. As noted above, the hot inert gas containing the stripped contaminants is referred to as the concentrated waste gas stream after it exits regenerator vessel 16A through top center opening 16B and enters concentrated waste gas stream outlet pipe 36. From outlet pipe 36 the concentrated waste gas stream is conveyed to a side inlet on enclosed ground flare 38 through pipe 37 and into an enclosed ground flare burner 38A, which is ignited by an enclosed ground flare burner pilot 38A. A spark ignition is used to ignite enclosed ground flare burner pilot 38A, which burns an admixture of air and propane. The propane gas for enclosed ground flare burner pilot 38A is supplied from a compressed propane cylinder 39 through a motorized and automated enclosed ground flare pilot gas supply valve 74B and the enclosed ground flare burner pilot propane pipe. Simultaneously, purified biogas enters enclosed ground flare 38 through enclosed ground flare purified biogas inlet 41A, which is fed by the enclosed ground flare burner purified biogas pipe 41. Upstream of enclosed ground flare burner purified biogas inlet 41A, and located on enclosed ground flare burner purified biogas pipe 41 is a flame arrestor 44, which is preceded by a motorized automated flow control valve 69, which is in turn preceded by a motorized automated "Open/Close" purified biogas flow valve 70. Simultaneously with the importation of the concentrated waste gas stream and the purified biogas stream is the conveyance of combustion air into enclosed ground flare 38 by an enclosed ground flare combustion air blower 42. Enclosed ground flare burner 38A mixes and combusts the concentrated waste gas stream, the purified biogas, and the combustion air to effectively destroy more than 99% of the contaminants in the concentrated waste gas stream. The resulting combustion gases are vented from enclosed ground flare 38 to the atmosphere through an exhaust stack 45. The energy required for the destruction of the contaminants is partially supplied by the concentrated waste gas stream itself and partially supplied by the purified biogas stream. This combination of two fuel sources from within the system itself yields an extremely low energy cost for destruction of the contaminants (i.e., a low parasitic load).

Instrumentation and Controls

An integral part of the Biogas Purification System described above is full automation by the use of three separate but interlinked PLCs. These include PLC 83 for controlling enclosed ground flare 38, PLC 84 for controlling IGG 31, and PLC 85, which interlinks the other PLCs and provides other required automation (such as control of the rotary valves responsible for transferring spent filter media to the regeneration vessel, and transferring regenerated filter media to the filter/concentrator vessel).

The PLCs control the startup and shutdown of the Biogas Purification System, the operation of IGG 31, the operation of enclosed ground flare 38, the operation of all fan and blower motors, and the operation of all motorized valves. While manual valves are utilized in the system (i.e., a concentrator media drain valve 76 and a regenerator media drain valve 75), the manual valves are used only if media is required to be removed from the system during a shutdown, and do not control the operation of any of the critical functions. PLCs therefore control all gas flows, gas temperatures, gas pressures, and gas oxygen levels within the entire system.

FIG. 5A schematically illustrates inputs logically coupled to PLC 83, which controls enclosed ground flare 38. PLC 83 operates enclosed ground flare combustion air blower 42 using a signal from a sensor 67. PLC 83 operates purified biogas flow valve 69 using a signal from a sensor 68. PLC 83 operates purified biogas flow control valve 70 using a signal from a sensor 71. PLC 83 operates enclosed ground flare pilot gas supply valve 74B using a signal from a sensor 74A. PLC 83 also monitors the temperature of the exhaust gas exiting the enclosed ground flare through a sensor 73. The input from sensor 73 causes PLC 83 to modulate the gas flow at purified biogas flow control valve 70, and causes PLC 83 to modulate the combustion air flow from enclosed ground flare combustion air blower 42. Such modulation controls the temperature to range from about 1600° F. to about 1900° F., to assure a greater than 99% destruction of the contaminants in the concentrated waste gas stream is achieved. PLC 83 also monitors enclosed ground flare burner 38A for a flame through a sensor 66. In the absence of a flame, PLC 83 will shut down the enclosed ground flare by closing enclosed ground flare pilot gas supply valve 74B, turning off enclosed ground flare combustion air blower 42, and closing purified biogas control valve 69 (preferably in that order) for safety. PLC 83 will also send a signal to main biogas purification PLC 85 to divert the concentrated waste gas stream to a bypass pipe (not shown) so that it is no longer conveyed to the enclosed ground flare.

FIG. 5B schematically illustrates inputs logically coupled to PLC 84, which controls IGG 31. PLC 84 for IGG 31 operates all functions of the IGG through an on-board processor that conforms to NFPA standards. This on-board processor controls the purified biogas and combustion air flows to the pilot burner and main burner and compensates for fluctuating methane concentrations in purified inert gas generator combustion air blower 33. PLC 84 accomplishes these tasks using signals from various sensors, and sending control inputs to various components, including, a hot inert gas generator outlet temperature sensor 35, a hot inert gas fan on/off switch 63, an ultraviolet (UV) sensor 64 for the inert gas generator burner, inert gas generator combustion air blower 65, a valve 60 for supplying purified biogas to IGG 31, and a motor 59 configured to actuate valve 60.

FIG. 5C schematically illustrates inputs logically coupled to Main Biogas Purification System PLC 85, which monitors the temperature of the incoming biogas through a sensor 52A, and the heated biogas temperature at a sensor 52B, and controls the temperature of the incoming biogas exiting heat exchanger 2. This is accomplished by modulating a hot air supply valve 81 using a signal from a sensor 82. Hot air blower 48 is turned on or off using a signal from a sensor 77, which is linked to Main Biogas Purification System PLC 85. A rate of regenerated media flowing into concentrator vessel 4 at inlet 20B is modulated by a rotary gas lock valve 25, which communicates with Main Biogas Purification System PLC 85 via a sensor 53. The rate of spent media flowing from concentrator vessel 4 is modulated by a rotary gas lock valve 11, which communicates with Main Biogas Purification System PLC 85 via a sensor 54. Both rotary gas lock valves are modulated by a signal that originates from high and low spent media level sensors 61 and 62. Pneumatic blower 78 is controlled (i.e. turned on or off) using a signal from Main Purification System PLC 85 via a sensor 55. A regenerator temperature sensor 56, a regenerator oxygen level sensor 57, and a concentrated waste gas pressure sensor 58 are interlinked between Main Purification System PLC 85, IGG PLC 84, and enclosed ground flare PLC 83. Preferably each input linked to PLC 83 and 84 is also linked directly to PLC 85.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A process for removing organosilicon and halogenated contaminants from a gas stream to achieve a clean fuel gas, comprising the steps of:
   (a) passing the gas stream through a filter vessel including a filter media configured to remove organosilicon and halogenated contaminants from the gas stream, thereby producing a clean fuel gas and spent filter media;
   (b) removing a portion of the spent filter media from the filter vessel;
   (c) using a portion of the clean fuel gas to generate a hot inert gas;
   (d) using the hot inert gas to remove contaminants from the spent filter media, thereby regenerating the filter media;
   (e) returning the regenerated filter media to the filter vessel; and
   (f) using a portion of the clean fuel gas to treat the contaminants removed from the spent filter media, such that an exhaust from treating the contaminants is discharged without contacting the spent filter media.

2. The method of claim 1, wherein the step of passing the gas stream through a filter vessel including a filter media configured to remove organosilicon and halogenated contaminants from the gas stream comprises the step of directing the gas stream upward through the filter media.

3. The method of claim 2, wherein the step of removing a portion of the spent filter media from the filter vessel comprises the step of removing spent filter media from a lower portion of the filter vessel, such that a direction of a motion of the spent filter media substantially opposes a direction of the gas stream.

4. The method of claim 1, wherein the step of using the hot inert gas to remove contaminants from the spent filter media, thereby regenerating the filter media, comprises the step of directing the hot inert gas upward through the spent filter media.

5. The method of claim 4, wherein the step of returning the regenerated filter media to the filter vessel comprises the step of removing regenerated filter media from a lower portion of a regeneration vessel, such that a direction of a motion of the regenerated filter media substantially opposes a direction of the hot inert gas.

6. A process for removing organosilicon and halogenated contaminants from a gas stream to achieve a clean fuel gas, comprising the steps of:
   (a) passing the gas stream through a filter media configured to remove organosilicon and halogenated organic contaminants from the gas stream, the filter media being contained within a first volume;
   (b) collecting a clean fuel gas exiting from the first volume the clean fuel gas being substantially free of the organosilicon and halogenated organic contaminants;
   (c) removing spent filter media loaded with the organosilicon and halogenated organic contaminants from the first volume and directing them into a second volume;
   (d) using a portion of the clean fuel gas collected from the first volume to generate a hot inert gas, the hot inert gas being substantially free of the organosilicon and halogenated organic contaminants;
   (e) directing the hot inert gas into the second volume to remove contaminants from the spent filter media, thereby regenerating the filter media, such that substantially all of the energy required to remove the contaminants is provided by the hot inert gas;
   (f) collecting a first exhaust gas from the second volume, the first exhaust gas including the organosilicon and halogenated organic contaminants;
   (g) using a portion of the clean fuel gas collected from the first volume to treat the halogenated organic contaminants removed from the spent filter media in the first exhaust gas, thereby generating a second exhaust gas including the organosilicon contaminants; and
   (h) preventing the organosilicon contaminants from depositing undesirable silicates in the second volume by discharging the second exhaust gas without allowing the second exhaust gas to enter the second volume.

7. A system for removing organosilicon and halogenated contaminants from a gas stream to achieve a clean fuel gas, comprising:

(a) a filter vessel including a filter media configured to remove organosilicon and halogenated contaminants from the gas stream, thereby producing a clean fuel gas and spent filter media;

(b) a regeneration vessel configured to remove contaminants from spent filter media;

(c) a filter media transfer subsystem configured to transfer spent filter media from the filter vessel to the regeneration vessel, and to transfer regenerated filter media from the regeneration vessel to the filter vessel;

(d) a hot inert gas generator configured to use a portion of the clean fuel gas to generate a hot inert gas, the hot inert gas generator being coupled in fluid communication with the filter vessel to receive the clean fuel gas, and with the regeneration vessel, to direct hot inert gas into the regeneration vessel to regenerate the spent filter media; and (e) a flare subsystem configured to use a portion of the clean fuel gas to treat contaminants removed from the spent filter media by the hot inert gas, the flare subsystem being coupled in fluid communication with the filter vessel to receive the clean fuel gas, and with the regeneration vessel to receive the hot inert gas loaded with contaminants removed from the regenerated filter media, the flare subsystem being configured to discharge exhaust from treating the contaminants without allowing the exhaust to contact the spent filter media.

8. The system of claim 7, further comprising a pressure lock volume configured to maintain high pressure conditions in the filter vessel, the pressure lock volume comprising:

(a) a volume selectively coupled in fluid communication with the filter vessel and the regeneration vessel;

(b) a first valve configured to selectively couple the volume in fluid communication with the filter vessel; and (c) a second valve configured to selectively couple the volume in fluid communication with the regeneration vessel.

9. A system for removing organosilicon and halogenated contaminants from a gas stream to achieve a clean fuel gas, comprising:

(a) a filter vessel including a filter media configured to remove organosilicon and halogenated contaminants from the gas stream, thereby producing a clean fuel gas and spent filter media;

(b) a regeneration vessel configured to remove contaminants from spent filter media;

(c) a filter media transfer subsystem configured to transfer spent filter media from the filter vessel to the regeneration vessel, and to transfer regenerated filter media from the regeneration vessel to the filter vessel;

(d) a hot inert gas generator configured to use a portion of the clean fuel gas to generate a hot inert gas, the hot inert gas generator being coupled in fluid communication with the filter vessel to receive the clean fuel gas, and with the regeneration vessel, to direct hot inert gas into the regeneration vessel to regenerate the spent filter media;

(e) a flare subsystem configured to use a portion of the clean fuel gas to treat contaminants removed from the spent filter media by the hot inert gas, the flare subsystem being coupled in fluid communication with the filter vessel to receive the clean fuel gas, and with the regeneration vessel to receive the hot inert gas loaded with contaminants removed from the regenerated filter media; and (f) a pressure lock volume configured to maintain high pressure conditions in the filter vessel, the pressure lock volume comprising:

(i) a volume selectively coupled in fluid communication with the filter vessel and the regeneration vessel;

(ii) a first valve configured to selectively couple the volume in fluid communication with the filter vessel; and (iii) a second valve configured to selectively couple the volume in fluid communication with the regeneration vessel.

10. The method of claim 6, wherein the step of using a portion of the clean fuel gas to generate a hot inert gas comprises the step of using a first combustor to generate the hot inert gas, and the step of using a portion of the clean fuel gas to treat the contaminants removed from the spent filter media comprises the step of using a different combustor to treat the contaminants.

11. The method of claim 6, wherein the step of using a portion of the clean fuel gas to treat the contaminants removed from the spent filter media comprises the step of discharging the exhaust from the treatment of the contaminants removed from the spent filter media, without allowing the exhaust to contact the spent filter media.

12. The method of claim 6, wherein the step of using the hot inert gas to remove contaminants from the spent filter media, thereby regenerating the filter media comprises the step of removing the contaminants such that substantially all of the energy required to remove the contaminants is provided by the hot inert gas.

13. The method of claim 1, further comprising the step of using a pressure lock volume when removing the portion of the spent filter media from the filter vessel and returning the regenerated filter media to the filter vessel, the pressure lock volume being configured to maintain high pressure conditions in the filter vessel.

14. A system for removing organosilicon and halogenated contaminants from a gas stream to achieve a clean fuel gas, comprising:

(a) a filter vessel including a filter media configured to remove organosilicon and halogenated contaminants from the gas stream, thereby producing a clean fuel gas and spent filter media;

(b) a regeneration vessel configured to remove contaminants from spent filter media;

(c) a filter media transfer subsystem configured to transfer spent filter media from the filter vessel to the regeneration vessel, and to transfer regenerated filter media from the regeneration vessel to the filter vessel;

(d) a hot inert gas generator configured to use a portion of the clean fuel gas to generate a hot inert gas, the hot inert gas generator being coupled in fluid communication with the filter vessel to receive the clean fuel gas, and with the regeneration vessel, to direct hot inert gas into the regeneration vessel to regenerate the spent filter media, such that substantially all of the energy required to remove the contaminants is provided by the hot inert gas directed through the regeneration vessel; and (e) a flare subsystem configured to use a portion of the clean fuel gas to treat contaminants removed from the spent filter media by the hot inert gas, the flare subsystem being coupled in fluid communication with the filter vessel to receive the clean fuel gas, and with the regeneration vessel to receive the hot inert gas loaded with contaminants removed from the regenerated filter media.

* * * * *

UNITED STATES PATENT AND TRADEMARK OFFICE
CERTIFICATE OF CORRECTION

PATENT NO. : 7,410,524 B2 Page 1 of 1
APPLICATION NO. : 11/233479
DATED : August 12, 2008
INVENTOR(S) : Tower et al.

It is certified that error appears in the above-identified patent and that said Letters Patent is hereby corrected as shown below:

Title Page
Section (76) - Inventors    delete "Lowell E. Howard, 11206 167th Ct. NE., Redmond, WA (US) 98052;"

Signed and Sealed this

Twenty-first Day of October, 2008

JON W. DUDAS
*Director of the United States Patent and Trademark Office*